US00PP28765P2

(12) United States Plant Patent
Pavlich

(10) Patent No.: US PP28,765 P2
(45) Date of Patent: Dec. 12, 2017

(54) ***BEGONIA* PLANT NAMED 'ENCHANTED MOONLIGHT'**

(50) Latin Name: ***Begonia* hybrid**
Varietal Denomination: Enchanted Moonlight

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,890

(22) Filed: Jul. 14, 2016

(51) Int. Cl.
*A01H 5/02* (2006.01)

(52) U.S. Cl.
USPC ..... Plt./343

(58) Field of Classification Search
USPC ..... Plt./343, 345
CPC ..... A01H 5/0238; A01H 5/02; A01H 5/00
See application file for complete search history.

(56) References Cited

PUBLICATIONS

Nursery Management Terra Nova Nurseries displays new varieties at 2016 California Spring Trials 2016, retrieved on Aug. 16, 2017, retrieved from the Internet at http://www.nurserymag.com/article/terra-nova-2016-trials/ 3 pp.*
Terra Nova Nurseries *Begonia* COCOA 'Enchanted Moonlight' retrieved on Aug. 16, 2017, retrieved from the Internet at http://www.terranovanurseries.com/growers/begoniacocoaenchantedmoonlight-p-817.html 2 pp.*

* cited by examiner

*Primary Examiner* — June Hwu
(74) *Attorney, Agent, or Firm* — Klarquist Sparkman, LLP

(57) ABSTRACT

A new and distinct form of *Begonia* plant characterized by attractive dark chocolate brown leaves with green veins, numerous large white flowers, an upright habit when young, becoming decumbent with maturity, an extremely long bloom time, and excellent vigor.

1 Drawing Sheet

Botanical denomination: *Begonia* hybrid.
Variety designation: 'Enchanted Moonlight'.

BACKGROUND OF THE INVENTION

The present invention relates to a new and distinct cultivar of *Begonia*, of the family Begoniaceae, and given the cultivar name, 'Enchanted Moonlight'. The new cultivar originated from a branch mutation of *Begonia* 'Enchanted Evening' (U.S. Plant Pat. No. 25,512) found in the nursery greenhouse in Canby, Oreg.

This selection is uniquely characterized by:

1. attractive dark chocolate brown leaves with green veins,
2. numerous large white flowers,
3. an upright habit when young, becoming decumbent with maturity,
4. an extremely long bloom time, and
5. excellent vigor.

Compared to the parent, *Begonia* 'Enchanted Evening' the new cultivar has a white flowers rather than coral-pink flowers.

Compared to the *Begonia* 'Unstoppable Upright White', the new cultivar is more stiffly upright with larger flowers with broader tepals and darker foliage.

The new variety has been reproduced only by asexual propagation (leaf and stem cuttings and tissue culture using growing tips). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of three month old plants of the new cultivar in 4 inch pots in a warm greenhouse in February in full bloom in Canby, Oreg.

FIG. 2 shows a six month old plant in full bloom in March in a 1 gallon container in a warm greenhouse in Canby, Oreg.

DETAILED PLANT DESCRIPTION

The following is a detailed description of the new *Begonia* cultivar based on observations of 5-month-old specimens grown in one gallon containers in a warm greenhouse in April in Canby, Oreg. The color descriptions are all based on *The Royal Horticultural Society Colour Chart,* 5$^{th}$ edition, 2007.

Plant:

*Type*.—Herbaceous perennial.
*Form*.—Upright when young, caulescent, becoming decumbent with maturity.
*Cold hardiness*.—USDA Zone 10.
*Size*.—Grows to 22 cm tall and 26 cm wide.
*Vigor*.—Excellent.

*Roots*.—Rooting initiates in two weeks, roots White NN155C in color.

Stem:

*Type*.—Upright in the first season, becoming decumbent with age.

*Size*.—Grows to 20 cm long and 1 mm wide (mature stems will grow to 50 cm long and 12 mm wide if left on the plant).

*Internodes*.—From 7 mm to 2 cm long.

*Surface*.—Glabrous.

*Color*.—Yellow Green 146A.

Leaf:

*Type*.—Simple.

*Arrangement*.—Alternate.

*Shape*.—Obliquely ovate to lanceolate.

*Leaf strength*.—Good.

*Margins*.—Serrate, slightly undulate, shallowly lobed, with 1 to 5 lobes.

*Apex*.—Acuminate.

*Base*.—Oblique and truncate.

*Venation*.—Palmate, Green 136B topside, bottom side Green 138C.

*Blade size*.—Grows to 5.4 cm wide and 12.5 cm long.

*Surface texture*.—Pubescent on top and glabrous on bottom.

*Stipules*.—Deciduous, ovate, 7 mm long and 5 mm wide, apex acute and cuspidate, base clasping, entire, both sides pubescent, both sides Yellow Green 145C with base Greyed Purple 187B.

*Petiole description*.—Grows to 6 cm long and 3 mm wide, succulent, pubescent, Yellow Green 152B.

*Leaf color*.—Top side closest to Greyed Purple N186A with veins Green 136B; bottom side closest to Greyed Purple 187, but duller, with veins Green 138C.

Inflorescence:

*Type*.—Axillary, bisexual, cymose.

*Number of flowers per cyme*.—2 to 3.

*Peduncle description*.—Grows 8 cm long and 4 mm wide, sparsely pubescent, moderately strong, Yellow Green 152B tinted Greyed Orange 175A on top side in higher light; with 2 opposite, dehiscent petiolate leaf-bracts below each cyme, broadly ovate to orbicular, cupped and overlapping, each grow to 16 mm wide and 14 mm long, margins serrate and ciliate, tip obtuse, base clasping, both sides glabrous, both sides Yellow Green 152D lightly tinted Greyed Orange 175A.

*Pedicel description*.—Grow to 35 mm long, 1.5 mm wide, pubescent, medium strength, Red 46B, except where shaded, Yellow Green 152B.

*Bloom period*.—Late winter to fall in Canby, Oreg.

Flower bud:

*Size*.—40 mm long and 30 mm wide prior to opening.

*Shape*.—Flat teardrop.

*Surface texture*.—Glabrous.

*Color*.—White 155D at tepal area, Yellow Green 144A on ovary.

Flower:

*Type*.—Monoecious, bilaterally symmetrical.

*Pistillate flower*.—Grows to 45 mm deep and 90 mm wide overall; 5 fleshy tepals, grow to 45 mm long and 28 mm wide, obovate, tip obtuse to acute, base cuneate, margins entire, glabrous on both sides, inside White N155D with pink tinge, N155C, near base, bottom side White N155D tinted Red Purple 63A on outer tepals; 1 pistil, 19 mm long overall, ovary to 20 mm wide and 11 mm deep, three winged, two equal and one longer, Yellow Green 145A tinted Greyed Red 179C on wings, style 3-branched, 8 mm deep and 12 mm wide overall, stigma 2-branched and twisted, stigma 5 mm deep and 5 mm wide overall, Yellow Orange 12C.

*Staminate flower*.—5.5 cm deep and 7 cm wide, glabrous and both sides White N155D lightly tinted at the base Red Purple 63A; 2 outer tepals, 55 mm long and 41 mm wide, broadly elliptic, margin entire, tip obtuse, base obtuse; 2 inner tepals, 45 mm long and 23 mm wide, obovate, margin entire, tip obtuse, base attenuate; stamen many in a globular head 12 mm in long and 10 mm deep, filaments 3 mm to 4 mm long, Yellow 19B, anthers 1 mm long and Yellow Orange 21A, pollen Yellow 19A.

*Fragrance*.—None.

*Lastingness*.—A cyme blooms for about 2 weeks on the plant, flowers are self-cleaning.

Fruit and seed: None seen.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

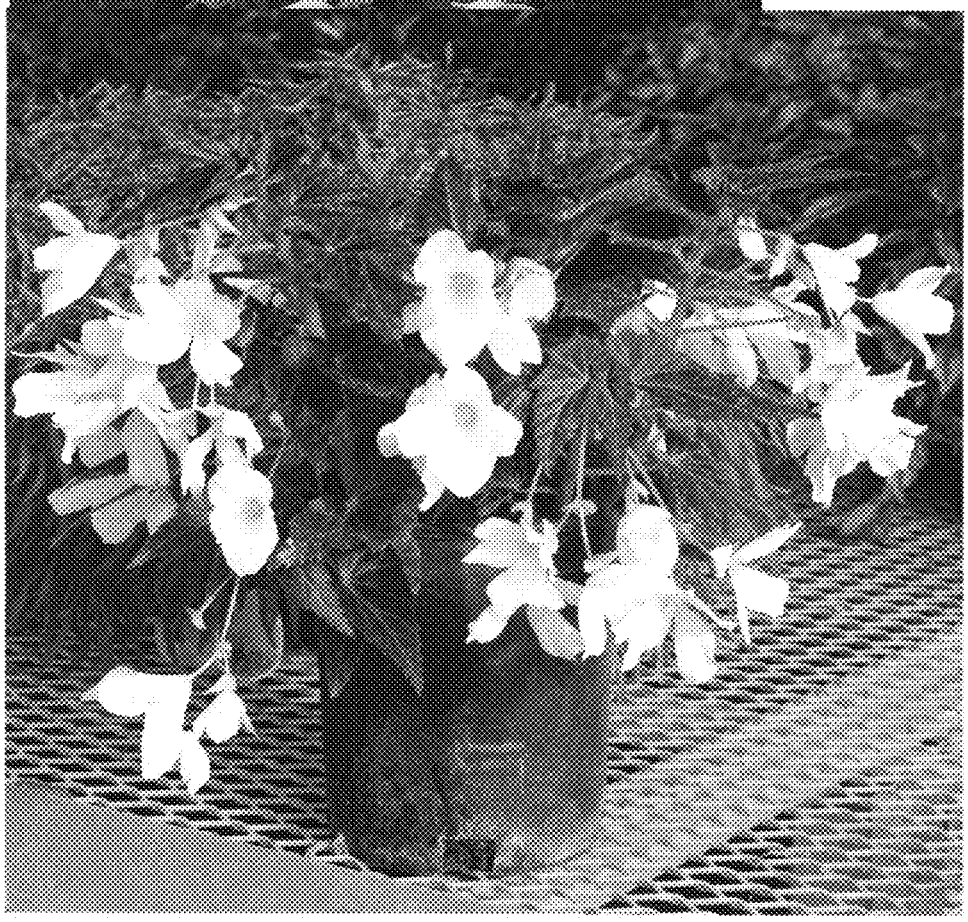

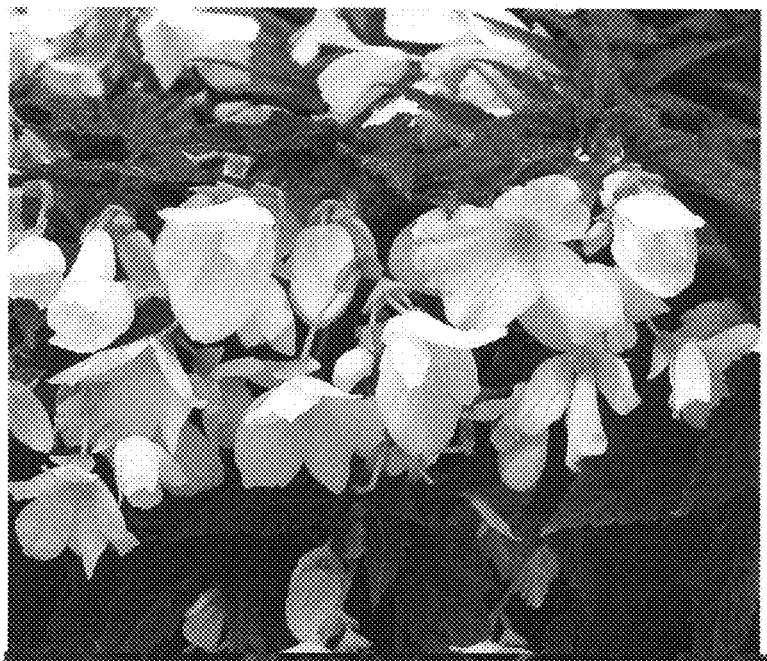
FIG. 1 left.
FIG. 2 below